(12) United States Patent
Boulanger et al.

(10) Patent No.: US 9,820,916 B2
(45) Date of Patent: Nov. 21, 2017

(54) DETECTION SYSTEM FOR FLOW CONTROL APPARATUS

(71) Applicant: Covidien LP, Mansfield, MA (US)

(72) Inventors: Jason Boulanger, Trenton, IL (US); Joseph Hudson, O'Fallon, MO (US); Lester Paul Trelford, St. Louis, MO (US)

(73) Assignee: Covidien LP, Mansfield, MA (US)

( * ) Notice: Subject to any disclaimer, the term of this patent is extended or adjusted under 35 U.S.C. 154(b) by 194 days.

(21) Appl. No.: 14/806,159

(22) Filed: Jul. 22, 2015

(65) Prior Publication Data

US 2016/0022545 A1 Jan. 28, 2016

Related U.S. Application Data

(60) Provisional application No. 62/028,983, filed on Jul. 25, 2014.

(51) Int. Cl.
*A61M 31/00* (2006.01)
*A61J 15/00* (2006.01)
(Continued)

(52) U.S. Cl.
CPC ......... *A61J 15/0076* (2015.05); *A61J 15/008* (2015.05); *A61J 15/0026* (2013.01);
(Continued)

(58) Field of Classification Search
CPC .. A61J 15/0026; A61J 15/0076; A61J 15/008; A61J 15/0088; A61J 2200/70;
(Continued)

(56) References Cited

U.S. PATENT DOCUMENTS 3,553,636 A 1/1971 Baird
3,738,156 A 6/1973 Bosselaar
(Continued)

FOREIGN PATENT DOCUMENTS

EP 1435511 A2 7/2004

OTHER PUBLICATIONS

International Search Report dated Dec. 4, 2015 in related International Application No. PCT/US2015/041510, 7 pages.
(Continued)

*Primary Examiner* — Jason Flick

(57) ABSTRACT

A flow control apparatus adapted to receive a feeding set includes a housing capable of receiving at least a portion of the feeding set. A pumping device is supported by the housing and positioned to contact the feeding set when the feeding set is received by the housing so the pumping device acts on the feeding set to produce fluid flow in the feeding set for delivery of fluid to a subject. An ultrasonic sensor is supported by the housing and arranged with respect to the pumping device to produce a sensor signal indicative of a viscosity of the fluid delivered through the feeding set. A control circuit is in communication with the ultrasonic sensor for receiving the sensor signal from the sensor indicative of the viscosity of the fluid and in communication with the pumping device to control operation thereof.

15 Claims, 11 Drawing Sheets

(51) Int. Cl.
*F04B 43/12* (2006.01)
*A61M 5/142* (2006.01)
*A61M 5/168* (2006.01)
*A61M 5/172* (2006.01)
*A61M 5/36* (2006.01)

(52) U.S. Cl.
CPC ...... *A61J 15/0088* (2015.05); *A61M 5/14232* (2013.01); *F04B 43/12* (2013.01); *A61M 5/14228* (2013.01); *A61M 5/168* (2013.01); *A61M 5/16804* (2013.01); *A61M 5/172* (2013.01); *A61M 5/365* (2013.01); *A61M 2205/14* (2013.01); *A61M 2205/3334* (2013.01); *A61M 2205/3375* (2013.01); *A61M 2205/6036* (2013.01)

(58) Field of Classification Search
CPC ...... A61M 2205/14; A61M 2205/3334; A61M 2205/3375; A61M 2205/6036; A61M 5/14228; A61M 5/14232; A61M 5/168; A61M 5/16804; A61M 5/172; A61M 5/365; F04B 43/12
USPC .......................................................... 604/67
See application file for complete search history.

(56) References Cited

U.S. PATENT DOCUMENTS

| | | | |
|---|---|---|---|
| 4,037,598 A | | 7/1977 | Georgi |
| 4,441,358 A | | 4/1984 | Osborne |
| 4,781,525 A | | 11/1988 | Hubbard et al. |
| 4,820,265 A | | 4/1989 | DeSatnick et al. |
| 4,872,813 A | | 10/1989 | Gorton et al. |
| 4,878,896 A | | 11/1989 | Garrison et al. |
| 4,967,797 A | | 11/1990 | Manska |
| 4,976,590 A | | 12/1990 | Baldwin |
| 5,135,026 A | | 8/1992 | Manska |
| 5,145,314 A | | 9/1992 | Westhoff, Jr. et al. |
| 5,176,631 A | | 1/1993 | Koenig |
| 5,460,490 A | | 10/1995 | Carr et al. |
| 5,522,799 A | | 6/1996 | Furukawa |
| 5,643,302 A | | 7/1997 | Beiser et al. |
| 5,720,721 A | * | 2/1998 | Dumas .............. A61M 5/16854 604/118 |
| 5,810,770 A | | 9/1998 | Chin et al. |
| 5,926,096 A | | 7/1999 | Mattar et al. |
| 6,022,195 A | | 2/2000 | Gaudet et al. |
| 6,098,466 A | | 8/2000 | Shkarlet |
| 6,227,040 B1 | | 5/2001 | Hastings et al. |
| 6,711,958 B2 | | 3/2004 | Bitto et al. |
| 6,852,094 B2 | | 2/2005 | Beck et al. |
| 7,497,116 B2 | | 3/2009 | Miyakoshi et al. |
| 7,704,227 B2 | | 4/2010 | Moberg et al. |
| 7,748,256 B2 | | 7/2010 | Yu et al. |
| 7,748,964 B2 | | 7/2010 | Yaegashi et al. |
| 7,753,880 B2 | | 7/2010 | Malackowski |
| 7,762,989 B2 | | 7/2010 | Simpson |
| 7,789,850 B2 | | 9/2010 | Roger |
| 7,879,026 B2 | | 2/2011 | Estes et al. |
| 8,006,570 B2 | | 8/2011 | Nazarifar et al. |
| 8,057,434 B2 | | 11/2011 | Burroughs et al. |
| 8,154,417 B2 | | 4/2012 | Hauenstein et al. |
| 8,342,811 B2 | | 1/2013 | Berwanger |
| 8,343,100 B2 | | 1/2013 | King et al. |
| 8,348,879 B2 | | 1/2013 | Gao et al. |
| 8,386,042 B2 | | 2/2013 | Yudovsky et al. |
| 2002/0151838 A1 | | 10/2002 | Beck et al. |
| 2004/0065143 A1 | * | 4/2004 | Husher .................. G01N 11/04 73/64.53 |
| 2004/0213677 A1 | | 10/2004 | Matzner et al. |
| 2008/0224852 A1 | | 9/2008 | Dicks et al. |
| 2010/0082011 A1 | | 4/2010 | Lewis et al. |
| 2010/0092307 A1 | | 4/2010 | Malakhova et al. |
| 2010/0152563 A1 | | 6/2010 | Turner et al. |
| 2010/0228222 A1 | | 9/2010 | Williams et al. |
| 2010/0228224 A1 | | 9/2010 | Pyles et al. |
| 2010/0241063 A1 | | 9/2010 | Straessler et al. |
| 2011/0088483 A1 | | 4/2011 | Will et al. |
| 2011/0246124 A1 | | 10/2011 | Lill et al. |
| 2011/0264045 A1 | | 10/2011 | Thompson et al. |
| 2012/0035535 A1 | | 2/2012 | Johnson et al. |
| 2012/0051945 A1 | | 3/2012 | Orndorff et al. |
| 2012/0067542 A1 | | 3/2012 | Frach et al. |
| 2012/0209165 A1 | | 8/2012 | Degen et al. |
| 2012/0302991 A1 | | 11/2012 | Blomquist et al. |
| 2013/0030405 A1 | | 1/2013 | Hartman et al. |
| 2013/0071272 A1 | | 3/2013 | Juretich et al. |
| 2013/0310756 A1 | * | 11/2013 | Whalley .................. A61M 5/31 604/189 |

OTHER PUBLICATIONS

Written Opinion of the International Searching Authority dated Dec. 4, 2015 in related International Application No. PCT/US2015/041510, 10 pages.

* cited by examiner

DETECTION SYSTEM FOR FLOW CONTROL APPARATUS

CROSS-REFERENCE TO RELATED APPLICATION

This application claims the benefit of priority to U.S. patent application Ser. No. 62/028,983, titled DETECTION SYSTEM FOR FLOW CONTROL APPARATUS, filed on Jul. 25, 2014, which is incorporated herein by reference in its entirety for all purposes.

BACKGROUND

The present invention generally relates to a flow control apparatus capable of detecting a condition of a pump set mounted on the apparatus.

Administering fluids containing medicine or nutrition to a patient is generally well known in the art. Typically, fluid is delivered to the patient by a pump set received by a flow control apparatus, such as a pump, connected to a source of fluid which delivers fluid to a patient. A flow control apparatus of the prior art may also be capable of monitoring and detecting fluid flow conditions that can occur within the loaded administration feeding set during operation of the flow control apparatus. Generally, prior art flow monitoring systems that are capable of monitoring and detecting flow conditions may rely on a sensor arranged relative to the administration feeding set.

SUMMARY

In a first aspect, a flow control apparatus is adapted to receive a feeding set. The flow control apparatus can comprise a housing capable of receiving at least a portion of the feeding set; a pumping device supported by the housing and positioned to contact the feeding set when the feeding set is received by the housing so the pumping device acts on the feeding set to produce fluid flow in the feeding set for delivery of fluid to a subject; an ultrasonic sensor supported by the housing and arranged with respect to the pumping device to produce a sensor signal indicative of a viscosity of the fluid delivered through the feeding set; and a control circuit in communication with the ultrasonic sensor for receiving the sensor signal from the sensor indicative of the viscosity of the fluid and in communication with the pumping device to control operation thereof, the control circuit being configured to determine the viscosity of the fluid from the sensor signal and to operate the pumping device to produce a fluid flow rate based on the determined viscosity of the fluid delivered through the feeding set. The control circuit can be configured to determine the viscosity by analyzing an amplitude of the sensor signal. The control circuit can include a memory containing a lookup table associating sensor signal amplitude with viscosity. The pumping device can have a motor and a rotor. The motor can be adapted to rotate the rotor so that the rotor repeatedly contacts the feeding set to produce fluid flow through the feeding set. The control circuit can adjust a rotation rate of the rotor based on the viscosity of the fluid delivered through the feeding set. The control circuit can be configured to decrease the rotation rate of the rotor as the detected fluid viscosity increases.

In a further aspect, a flow control system can deliver fluid to a subject. The system can comprise a feeding set; and a flow control apparatus including a housing capable of receiving at least a portion of the feeding set; a pumping device supported by the housing and positioned to contact the feeding set when the feeding set is received by the housing so the pumping device acts on the feeding set to produce fluid flow in the feeding set for delivery of fluid to a subject; and an ultrasonic sensor arranged with respect to the pumping device to sense the feeding set when the feeding set is received by the housing, the ultrasonic sensor including an ultrasonic emitter configured to emit an ultrasonic signal and an ultrasonic detector configured to detect the ultrasonic signal; a portion of the feeding set being disposed in a path of the ultrasonic signal when the feeding set is received by the housing, the feeding set producing a predetermined signal detected by the ultrasonic detector indicative of a condition of the feeding set.

The flow control system can further comprise a control circuit in communication with the ultrasonic sensor and configured to identify the feeding set based on the sensor signal received from the ultrasonic sensor.

The control circuit can have a memory and be configured to inhibit operation of the pumping device if the feeding set identified based on the sensor signal does not match a feeding set identity stored in the memory.

The memory can contain stored identities of plural feeding sets.

In some cases, the control circuit can be configured to match the sensor signal with one of the stored identities and to operate the flow control apparatus based on the stored identity that matches the sensor signal.

The feeding set can comprise a tubing and a sensor component mounted on the tubing, the sensor component being disposed in the path of the ultrasonic signal when the feeding set is received by the housing, the sensor component being constructed to produce the predetermined signal.

The predetermined signal can be produced by one of a size, shape, or material of the sensor component.

In still a further aspect, a flow control apparatus can be adapted to receive a pump set for driving fluid flow through the pump set. The flow control apparatus can comprise a housing capable of receiving at least a portion of the pump set; a pumping device supported by the housing and positioned to contact the pump set when the pump set is received by the housing so the pumping device acts on the pump set to produce fluid flow in the pump set; and a sensor assembly supported by the housing and arranged with respect to the pumping device for detecting a condition of the pump set when the pump set is received by the housing, the sensor assembly comprising a single emitter for emitting a signal and a plurality of detectors for detecting the signal emitted by the single emitter, each detector being configured to detect a different condition of the pump set based on the signal detected by the detectors.

The flow control apparatus can further comprise at least two detectors, each detector detecting a pump set condition including one of whether the pump set is properly received by the housing, the type of pump set, and a viscosity of the fluid in the pump set.

The flow control apparatus can further comprise at least three detectors, each detector detecting a pump set condition including one of whether the pump set is properly received by the housing, the type of pump set, and a viscosity of the fluid in the pump set.

The sensor assembly can be an ultrasonic sensor assembly including a single ultrasonic emitter and a plurality of ultrasonic detectors.

In yet a further aspect, a flow control apparatus can be adapted to receive a pump set for delivering fluid through the pump set. The flow control apparatus can comprise a housing capable of receiving at least a portion of the pump set; a pumping device supported by the housing and positioned to contact the pump set when the pump set is received by the housing so the pumping device acts on the pump set to produce fluid flow in the pump set; and an emitter constructed and arranged with respect to the pumping device to emit a first signal in a first direction toward a first section of the pump set when the pump set is received by the housing, and to emit a second signal in a second direction different from the first direction toward a second section of the pump set, the first and second signals being used to indicate a condition of the pump set at the first and second sections.

The emitter can be disposed to emit the first signal toward an upstream portion of the pump set and to emit the second signal toward a downstream portion of the pump set when the pump set is received by the housing.

The emitter can be disposed between the upstream and downstream portions of the pump set when the pump set is received by the housing.

The flow control apparatus can further comprise a first detector arranged with respect to the emitter for detecting the first signal, and a second detector arranged with respect to the emitter for detecting the second signal.

The emitter can be disposed between the first and second detectors.

The flow control apparatus can further comprise a first detector arranged with respect to the emitter for detecting the first ultrasonic signal, and a second detector arranged with respect to the emitter for detecting the second ultrasonic signal, the signal detected by the detectors indicating the presence of fluid in the pump set.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
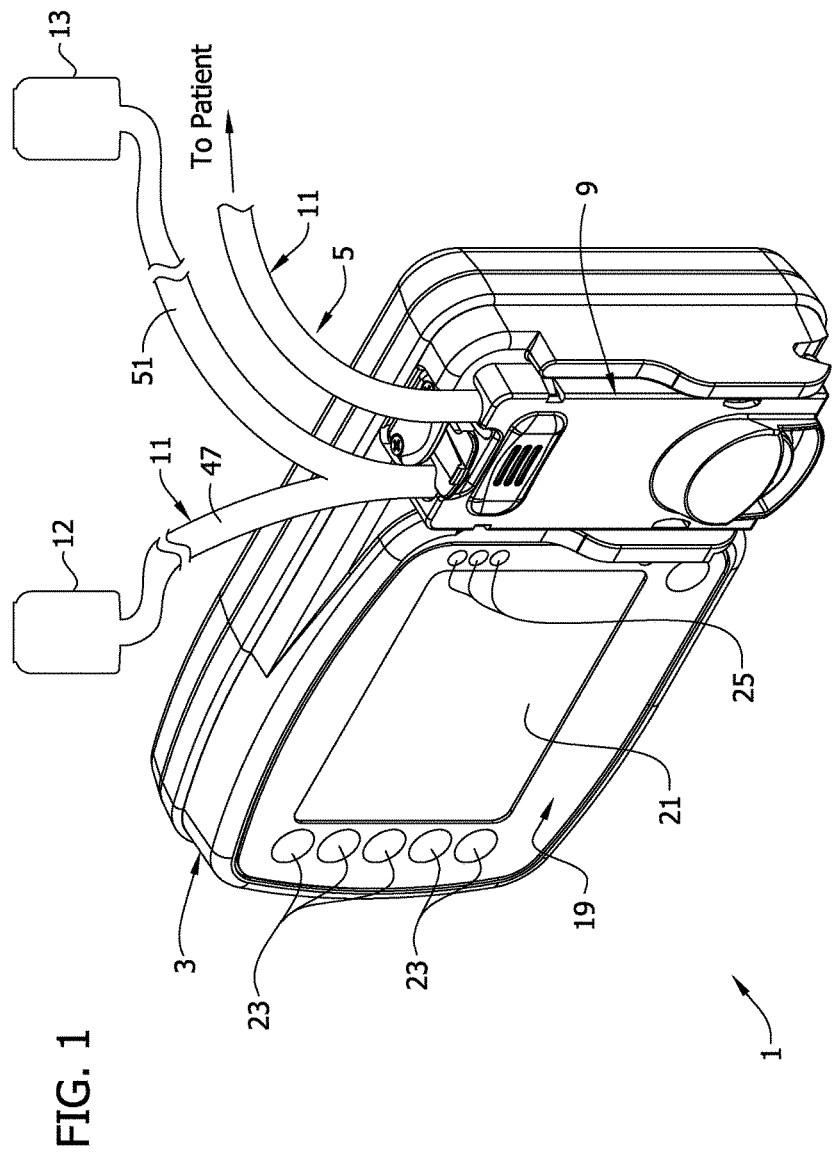
FIG. 1 is a perspective of an enteral feeding pump and a fragmentary portion of a feeding set (illustrated schematically) received on the pump.
Figure 2:
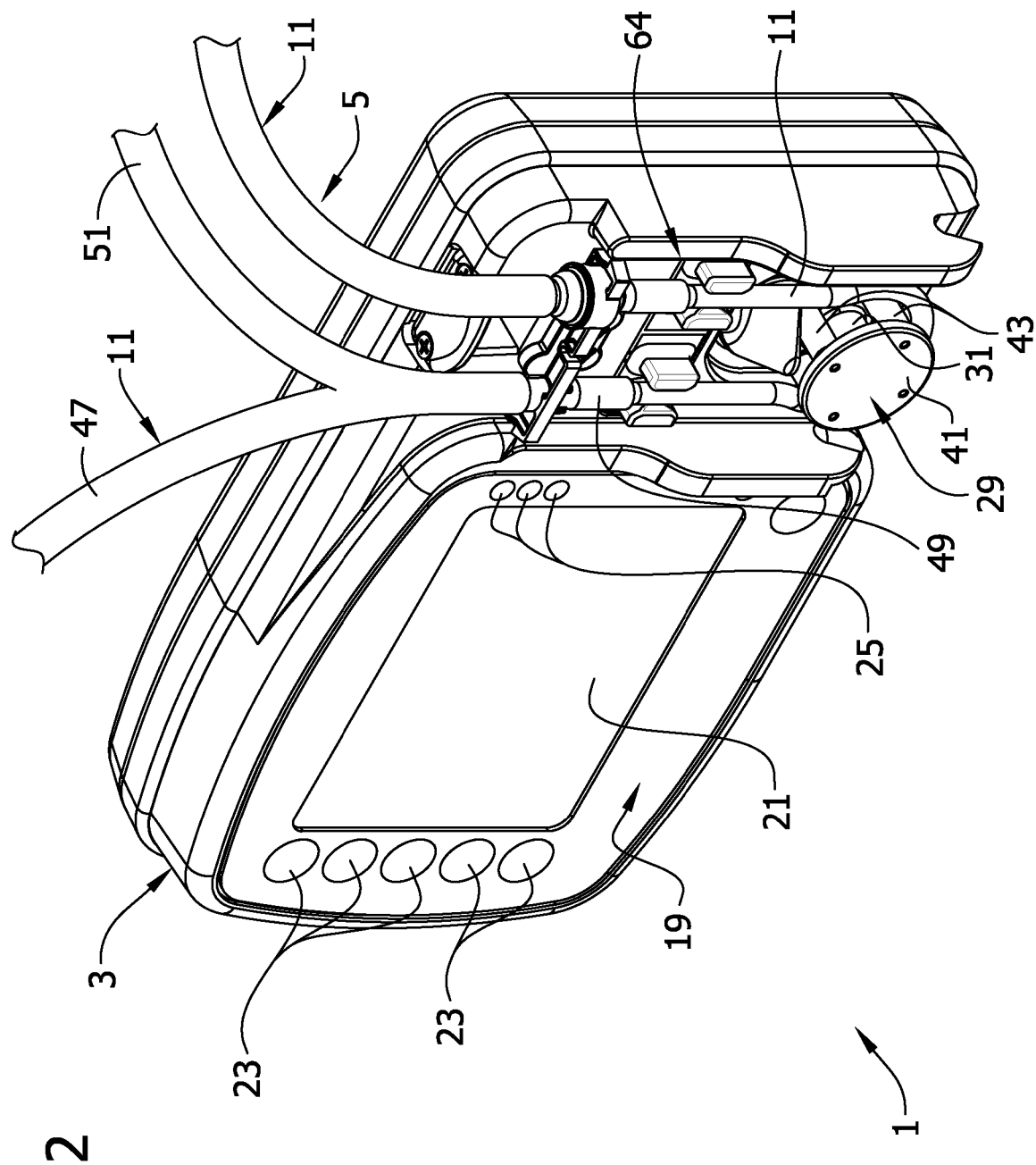
FIG. 2 is a perspective of FIG. 1 with a cassette housing of the feeding set removed.
Figure 3:
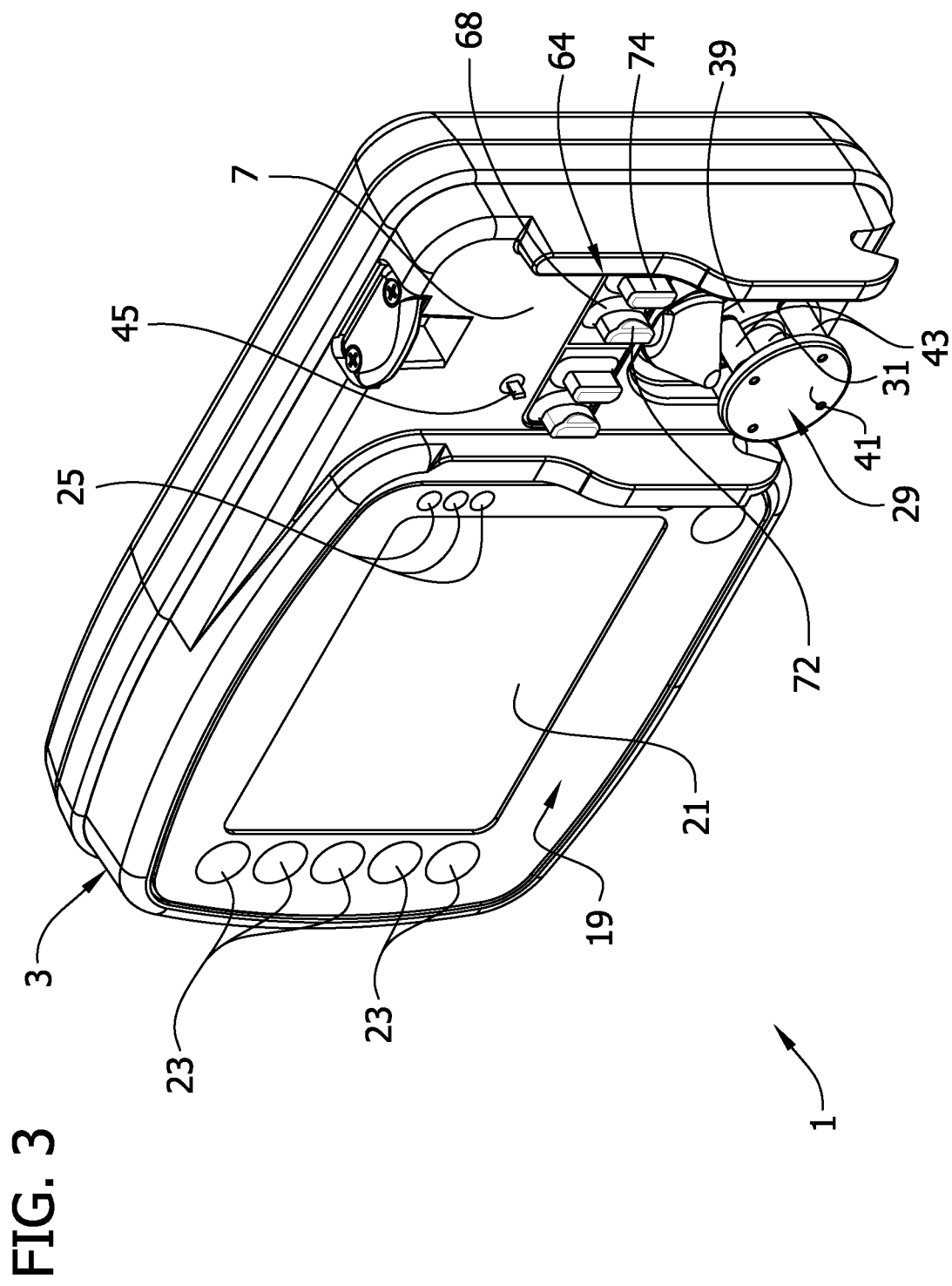
FIG. 3 is the perspective of FIG. 2 with the feeding set removed.

Referring now to the exemplary embodiment schematically illustrated in FIGS. 1-3, an enteral feeding pump (broadly, "a flow control apparatus") is generally indicated at 1. The pump 1 may comprise a housing 3 that is constructed so as to allow an administration feeding set 5 (broadly, "a pump set") to be mounted to the housing. As will be explained in greater detail below, the pump 1 may comprise a flow monitoring system 6 (FIG. 4) that is capable of detecting and identifying a condition of the feeding set 5 loaded on the pump. The housing 3 may comprise a recess 7 (FIG. 3) for receiving a cassette 9 of the feeding set 5 to load the feeding set on the pump. The feeding set 5 can comprise tubing indicated generally at 11 that provides a fluidic pathway between a bag 12 of nutritional liquid and a patient (FIG. 1). The tubing 11 may also provide a fluidic pathway between a bag 13 of flushing liquid. In one embodiment the flushing fluid may be water. The bags 12, 13 are shown schematically in FIG. 1. The cassette 9 may mount the tubing 11 for engaging the tubing with the pump 1 when the cassette is received in the recess 7. It will be understood that a pump set may have a construction other than shown herein without departing from the scope of the present disclosure. For example, a pump set (not shown) may not include a cassette 9 as illustrated herein.

As used herein, the feeding set 5 being "received" by the pump 1 means that the tubing 11 is engaged with the pump 1 so that the feeding set is ready for operation with the pump to deliver fluid to a patient. It will be appreciated that the term "housing," as used herein, may include many forms of supporting structures including, without limitation, multi-part structures and structures that do not enclose or house the working components of the pump 1.

The pump 1 may include a user interface 19 with a display screen indicated at 21 on the front of the housing 3 that is capable of displaying information about the status and operation of the pump. The pump 1 can further comprise buttons 23 and light emitting diodes 25 on the housing 3 for use with the display screen 21 to facilitate exchanging information, such as providing and obtaining information, between the pump 1 and a user. Various user interfaces for displaying information to the user and receiving user input may be implemented. Any of the various configurations of the user interface can involve utilizing one or more graphical display subcomponents. As an example, the display screen 21 may be a graphical user interface having a touch screen by which the user can provide the input information. In other embodiments, the user interface can be a tethered component that can be used to provide input information, provide operating information pertaining to the flow control apparatus, or both.

Figure 4:
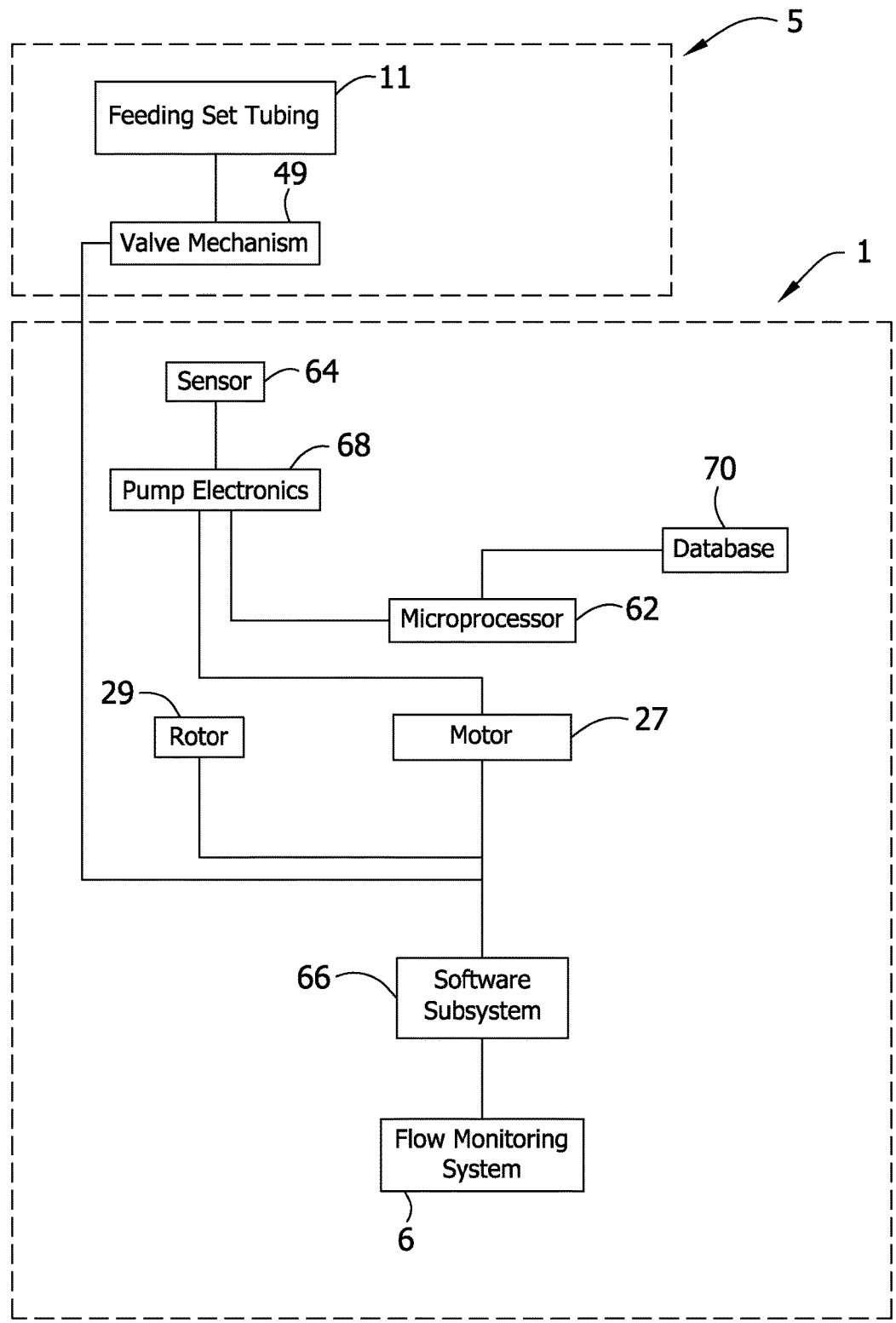
FIG. 4 is a block diagram illustrating elements of the pump including a flow monitoring system.

Referring to FIGS. 2-4, the pump 1 may include a pump motor 27 (FIG. 4) located in the housing 3. A pump rotor 29 may be mounted on a rotatable shaft 31 and rotated by the motor 27. In one embodiment, the pump rotor 29 includes an inner disk 39, an outer disk 41, and preferably a plurality of rollers 43 mounted between the inner and outer disks rotatable about their longitudinal axes relative to the disks.

The motor 27 may also be connected to a valve shaft 45 (FIG. 3). It will be understood that the valve shaft 45 could be omitted, or a separate motor (not shown) could be provided to operate the valve shaft. The rollers 43 may engage the feeding set 5 for moving fluid through the feeding set. In the illustrated embodiment, the pump motor 27, rotatable shaft 31, rotor 29, and optional valve shaft 45 may broadly be considered "a pumping device." These components may be individually considered "a pumping device." It will be understood that peristaltic pumps that use mechanisms other than rollers may fall within the scope of the present invention. However, other pumping devices (e.g., non-rotary devices) are envisioned.

As used herein, the portion of tubing 11 of the feeding set 5 from the bag 12, 13 leading to the rotor 29 is termed "upstream," while the portion of tubing 11 leading away from the rotor 29 to the patient is termed "downstream." Accordingly, rotation of the rotor 29 compresses the tubing 11 to drive fluid (e.g., a nutritional liquid) in a patient direction from the upstream to the downstream side of the feeding set 5. Although an exemplary feeding set 5 is shown, feeding sets of other configurations and other types of pump sets (not shown) can be used.

Referring now to FIGS. 1, 2 and 4, a first inlet tube section 47 is connected at an inlet of the tubing 11 to bag 12 of feeding fluid and to valve mechanism 49. A second inlet tube section 51 is connected at an inlet of the tubing 11 to bag 13 of flushing fluid and to the valve mechanism. The valve mechanism 49 is operable to selectively permit flow of feeding fluid from bag 12 or flushing fluid from bag 13, or prevent any fluid flow communication from the feeding or flushing fluid bags 12, 13 past the valve mechanism.

As previously stated, pump sets of different constructions may be used, for example a recertification set may be used to verify and/or correct the pump accuracy. The pump 1 can be configured to automatically recognize what kind of set is installed and to alter its operation to conform to that called for by the particular pump set. Still further, the pump 1 can be configured to recognize whether the tubing 11 is properly installed on the pump and determine a flow condition of the fluid in the pump set.

Referring to FIG. 2-4, the monitoring system 6 (FIG. 4) is capable of detecting and identifying a condition of the feeding set 5 loaded on the apparatus. The pump 1 may further comprise a microprocessor 62 in communication association with a sensor 64. The microprocessor 62 may control and manage the operation of the various components of the pump 1. A software subsystem 66 may be operatively associated with the microprocessor 62 and operatively associated with the monitoring system 6 to provide a means for the pump 1 to detect and identify a condition of the feeding set 5. It is to be understood that in the described embodiment, the flow monitoring system 6, the software subsystem 66, pump electronics 68, the microprocessor 62 and database 70 (broadly, "memory") may be broadly considered "a control circuit." These components may be individually considered "a control circuit." Moreover, other types of control circuits may be used within the scope of the present invention.

The sensor 64 may comprise an ultrasonic sensor. The sensor 64 may be located on the housing 3 of the pump 1 and positioned to detect the presence of fluid as well as one or more properties of a fluid in the feeding set 5, e.g., a viscosity of the fluid in the feeding set. In the illustrated embodiment, the sensor 64 is positioned in recess 7 and is adapted to securely receive the tubing 11 therein when the feeding set 5 is loaded on the pump 1. In order for the sensor 32 to detect the presence of fluid in the tubing 11 of the feeding set 5, the tubing may be engaged and retained within a sensor track 68 (FIG. 3) configured to receive the downstream side of the feeding set. Once the tubing 11 is engaged within the sensor track 68 and the remaining portions of the feeding set 5 are engaged with the pump 1, the monitoring system 6 may become operational. For example, the monitoring system 6 becomes operationally functional when a positive engagement of the tubing 11 within the sensor track 68 has been identified by the receipt of an acceptable signal, e.g., an ultrasonic signal, by one or more detectors or receivers.

Preferably, the sensor 64 may comprise an ultrasonic transmitter 72 that transmits an ultrasonic signal through the downstream portion of the tubing 11. The signal is directed towards and can be received by an ultrasonic receiver 74. Upon receipt of the ultrasonic signal, the receiver 74 may detect the presence of fluid within the tubing 11 and a viscosity of the fluid based on the characteristics of the ultrasonic signal received by the receiver 74 and communicated to the microprocessor 62.

The ultrasonic signal may detect the presence or absence of fluid in the tubing to give a basic indication of the operational status of the pump 1. The ultrasonic signal may be responsive to the presence of fluid in the tubing 11 such that fluid in the tubing will produce a decrease in amplitude of the signal as compared to a signal where fluid is not in the tubing. Further, a physical property of the fluid may be evaluated based on the signal from transmitter and modulated by the fluid and tubing, as received by the receiver. For example, a relative viscosity of the fluid can also be detected by the amplitude of the signal. In some cases, a fluid having a relatively low viscosity will cause a first signal amplitude, and the same fluid having a relatively high viscosity will cause a second signal amplitude that is lower than the first signal amplitude. The receiver 74 may then communicate with the microprocessor 62. Based on the characteristics of the received ultrasonic signal communicated to the microprocessor 62, the software subsystem 66 may determine whether fluid is present within the feeding set 5, and if fluid is present, a characteristic of the fluid, such as the relative viscosity of the fluid. For example, the database 70 may include a look up table for identifying a particular viscosity associated with a detected sensor signal amplitude. Other types of sensors for measuring one or more fluid properties or characteristics, including viscosity, other than ultrasonic sensors can be used. Additionally, the database 70 may store multiple predetermined signal amplitudes corresponding to various fluids and viscosities of the fluids. The flow monitoring system 6 may detect other conditions of the feeding set 5, the fluid within the feeding set, and the fluid coupled with the feeding set without departing from the scope of the disclosure.

The amount of fluid that is delivered to the subject is controlled by the number of rotations of the rotor 29 (in a counterclockwise direction as viewed in FIG. 2). In the illustrated embodiment, the rotor 29 includes the three rollers 43 so that each one-third of a rotation delivers one aliquot of fluid to the patient. As each roller 43 first engages the tubing 11, it pinches off the tubing thereby closing off an amount of fluid forward (i.e., toward the patient) from the fluid coming from the feeding fluid bag 12. The roller 43 continues to the right, pushing fluid forward of the roller toward the patient. Finally, the roller 43 releases engagement with the tubing 11 at about the same time the trailing roller engages the tubing for pinching it off for delivering the next aliquot of fluid. Thus, when the microprocessor 62 receives a command to deliver a selected fluid flow rate, it calculates the number of rotations within a given period of time that will deliver a number of aliquots producing the desired flow rate. It is to be understood that other ways of changing rotor operation could be used to maintain a constant flow rate. The selected flow rate may be a rate that is selected by the doctor, nurse or other care giver, or may be a default feeding rate pre-programmed into the pump 1.

To control the amount of fluid delivered to the subject accounting for the fluid viscosity, the microprocessor 62 can adjust a rate of rotation of the rotor 29, by adjusting an output of the motor 27. Thus, if the sensor 64 detects a fluid having a relatively high viscosity, which can be based on a predetermined baseline signal representative of a "normal" viscosity, the microprocessor 62 can decrease the output of the motor 27 decreasing the rate of rotation of the rotor 29 to more precisely pump a selected volume, thereby compensating for the high viscosity of the fluid. Conversely, if the sensor 64 detects a fluid having a relatively low viscosity, the microprocessor 62 can increase the output of the motor 27 increasing the rate of rotation of the rotor 29. Without the motor output adjustment, a relatively high viscosity fluid would not be dispensed in quantities of highest accuracy due to the high flow resistance caused by the viscosity of the fluid. In some embodiments, a low-viscosity fluid has a viscosity of less than about 100 cP, and a high-viscous fluid has a viscosity greater than or equal to about 75 cP. Accordingly, a "normal" viscous fluid may have a viscosity in a range of from about 25 cP and to about 74 cP. Signal amplitudes for a fluid within a viscosity in the normal range would not prompt the microprocessor 62 to adjust rotation of the rotor 29.

The sensor 64 may also detect a condition of the feeding set 5 separate from any fluid being delivered through the feeding set. Because the sensor 64 is positioned to direct the ultrasonic signal from the transmitter 72 through the tubing 11 of the feeding set 5, the receiver 74 may receive a signal specific to the feeding set. Thus, the signal received at the receiver 74 may be a result of the specific construction of the feeding set 5. In one instance, the feeding set 5 may produce a predetermined signal representative of a functional configuration of the feeding set. For instance, the signal detected by the receiver 74 may indicate the feeding set 5 as being one of a feed only, feed and flush, or recertification feeding set. Other functional configurations are also within the scope of the present disclosure. The database 70 may store multiple predetermined signals corresponding to various functional configurations.

Figure 5:
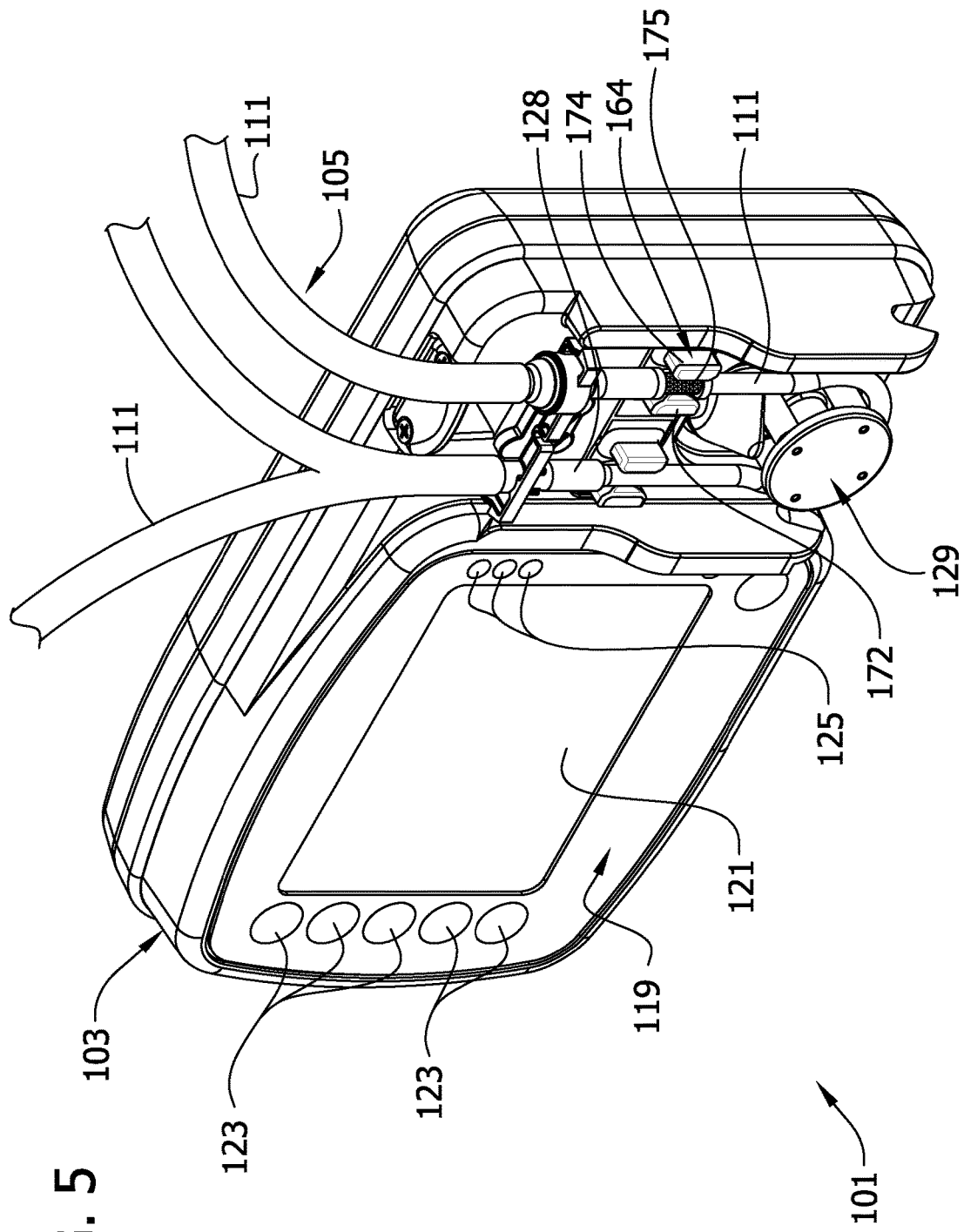
FIG. 5 is a perspective of another version of an enteral feeding pump and a fragmentary portion of a feeding set received on the pump with a cassette housing of the feeding set removed.
Figure 6:
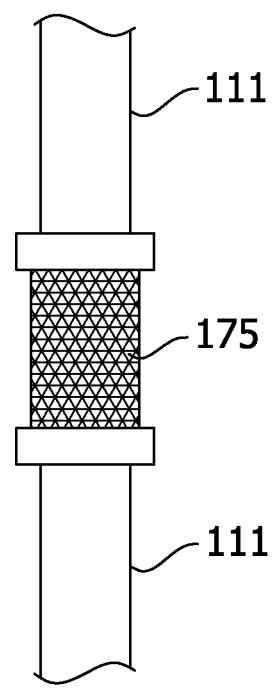
FIG. 6 is an illustration of a sensor component of the feeding set of FIG. 5.

Referring to FIGS. 5 and 6, a feeding set 105 of a second version may comprise a sensor component 175 in direct communication with tubing 111. In the illustrated embodiment, the sensor component is mounted on the tubing 111. The sensor component 175 may identify a functional configuration of the feeding set by producing a predetermined signal at receiver 174 indicating the associated functional configuration. A size, shape, or material of the sensor component 175 may determine the signal received by the receiver 174. Thus, a feeding set having a functional configuration comprising one of a feed only, flush and feed, or recertification configuration may have at least one of a different size, shape or material from another feeding set having a different functional configuration. For instance, a sensor component identifying a feeding set as having a feed only configuration may be formed from a first material having a first ultrasonic signal transmissive property. A sensor component identifying a feeding set as having a feed and flush configuration may be formed of a second material having a second ultrasonic signal transmissive property different from the first material. A sensor component identifying a feeding set as having a recertification configuration may be formed of a third material having a third ultrasonic signal transmissive property that is different from the first and second materials.

In another embodiment, a sensor component identifying a feeding set as having a feed only configuration may have a generally rectangular shape, a sensor component identifying a feeding set as having a feed and flush configuration may have a generally cylindrical shape, and a sensor component identifying a feeding set as having a recertification configuration may have a generally triangular shape. Other shapes are envisioned within the scope of the disclosure. Additionally, large, medium, and small sensor components may distinguish feeding sets having feed only, feed and flush, and recertification configurations. Moreover, some combination of size, shape and/or material may be sued for identification.

Figure 7:
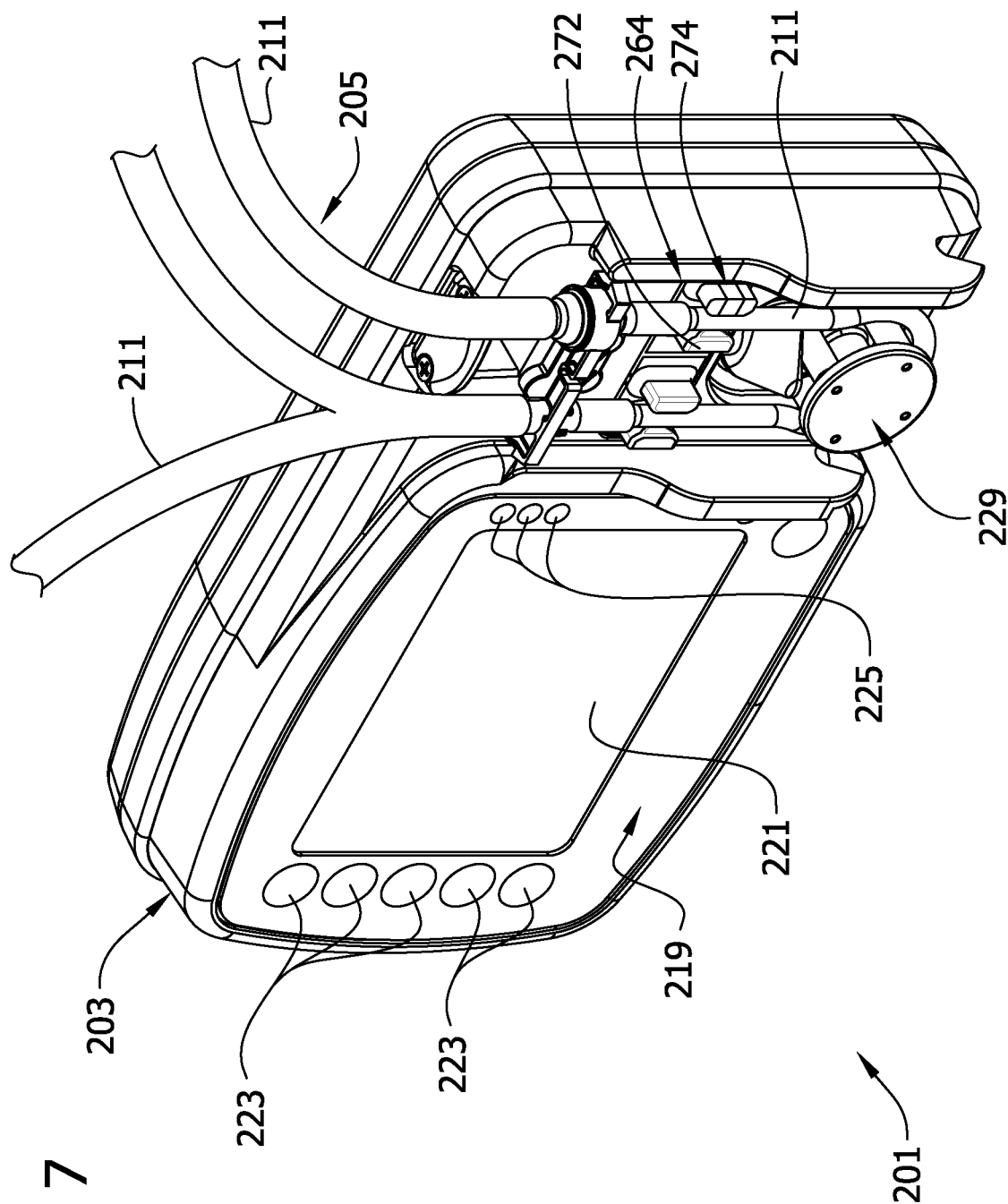
FIG. 7 is a perspective of still another version of an enteral feeding pump and a fragmentary portion of a feeding set received on the pump with a cassette housing of the feeding set removed.
Figure 8:
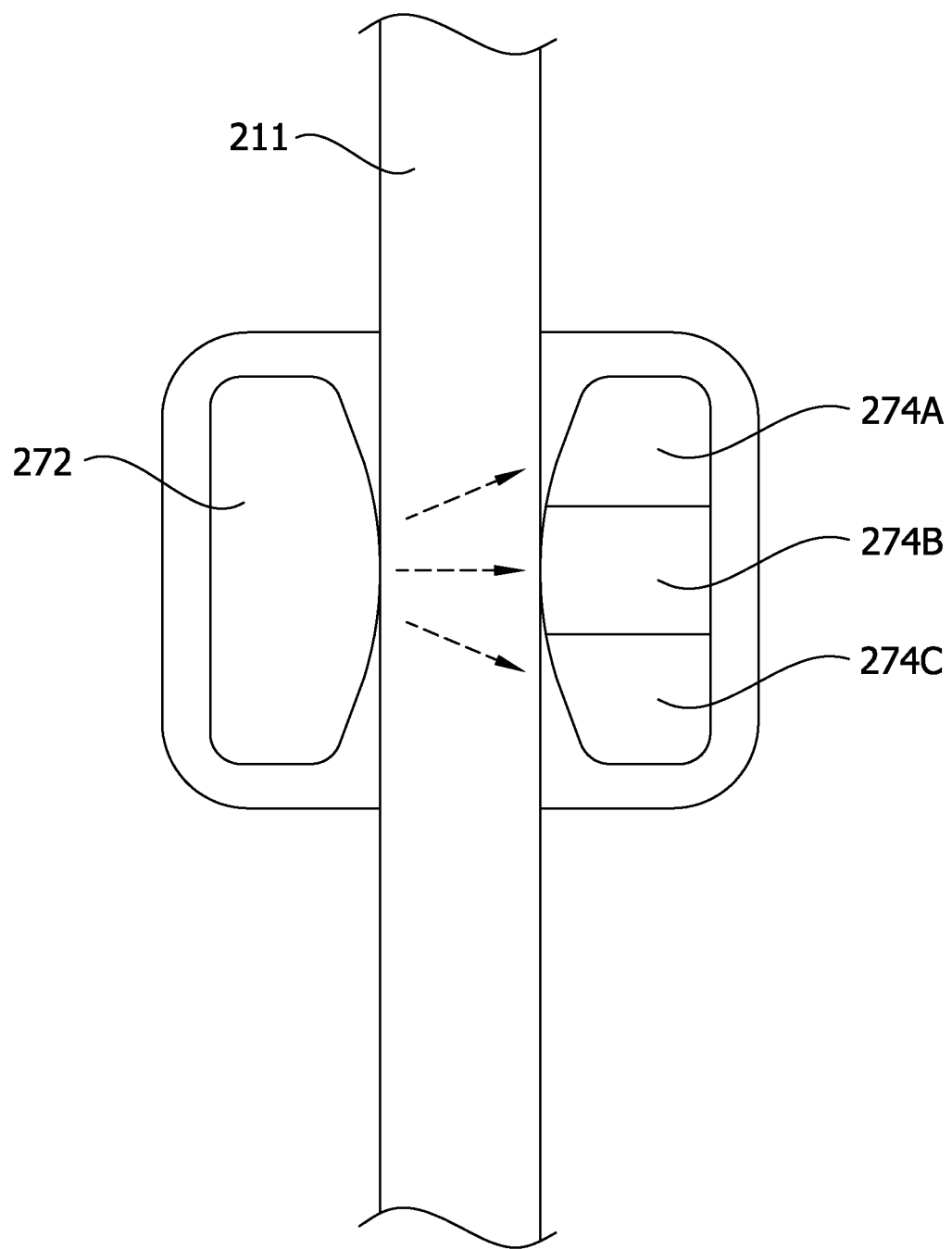
FIG. 8 is an illustration of a sensor of the pump of FIG. 7.

Referring to FIGS. 7 and 8, a pump 201 of a third version may comprise a sensor 264 including an ultrasonic transmitter 272 that transmits a broad ultrasonic signal through a downstream portion of tubing 211. The signals are directed towards and can be received by multiple ultrasonic receivers 274A, 274B, 274C. Upon receipt of the ultrasonic signals, the receivers 274A, 274B, 274C may detect a configuration of feeding set 205. Each receiver 274A, 274B, 274C may receive a signal indicative of a different condition of the feeding set 205. For instance, the signal received at receiver 274A may indicate proper loading of the feeding set 205, the signal received at receiver 274B may indicate the type of feeding set, and the signal received at receiver 274C may indicate a viscosity of the fluid in the feeding set. In the illustrated embodiment, three receivers 274 are shown. However, a different number of receivers 274 is within the scope of the present disclosure.

Figure 9:
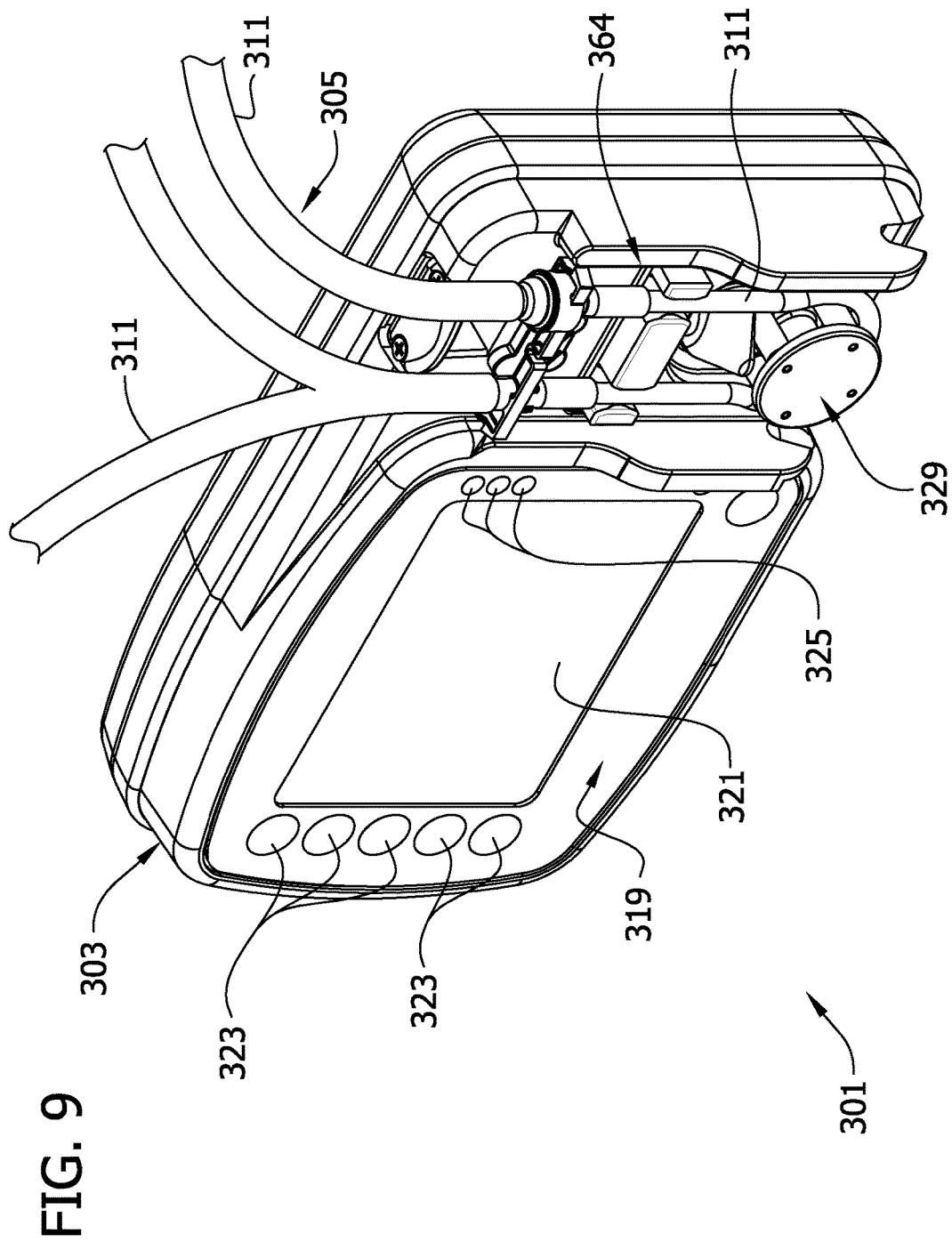
FIG. 9 is a perspective of yet another version of an enteral feeding pump and a fragmentary portion of a feeding set received on the pump with a cassette housing of the feeding set removed.
Figure 10:
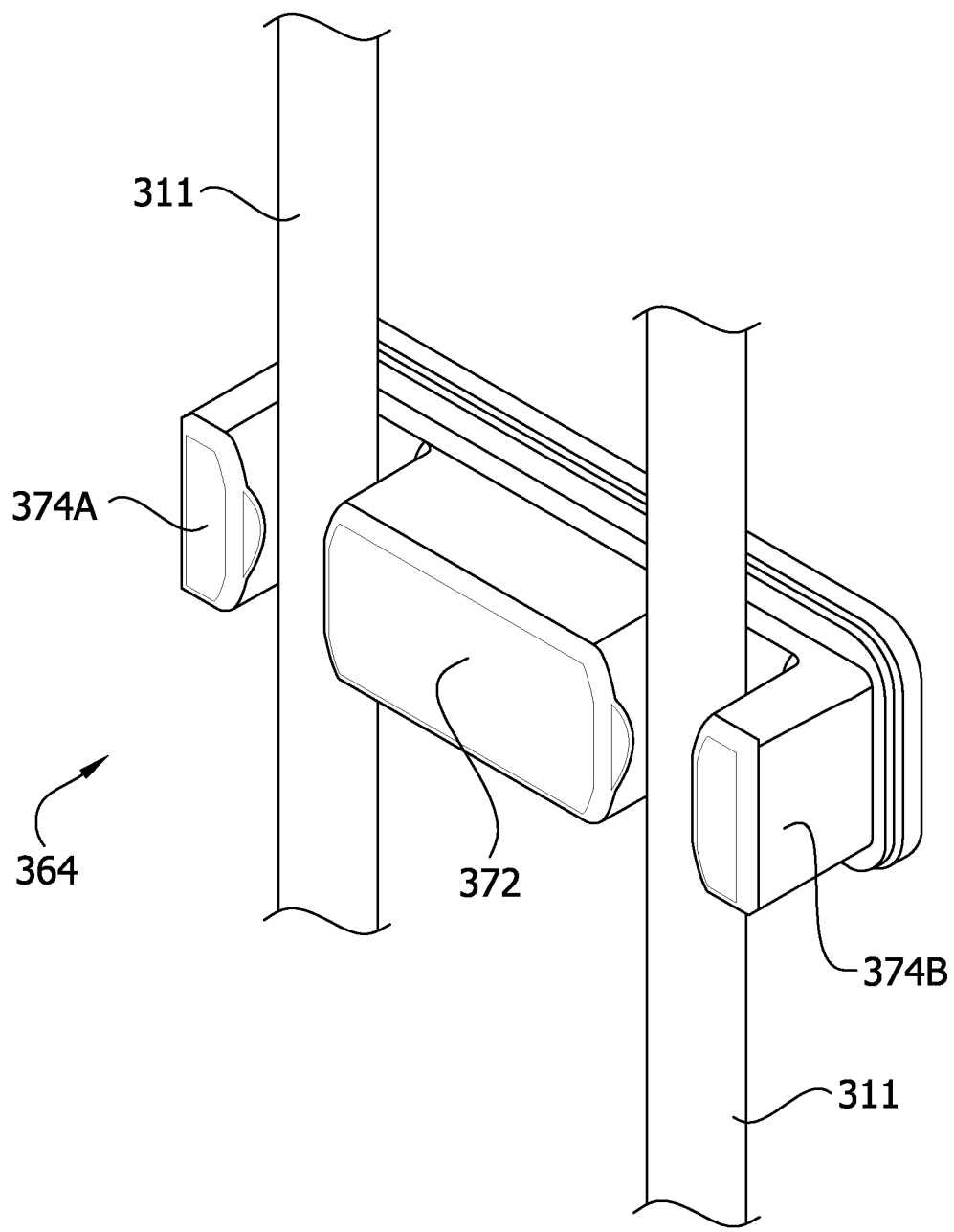
FIG. 10 is an enlarged perspective of a sensor of the pump of FIG. 9.

Referring to FIGS. 9 and 10, a pump 301 of a fourth version may comprise a sensor 364 including an ultrasonic transmitter 372 that transmits an ultrasonic signal in a first direction through an upstream portion of tubing 311 and transmits an ultrasonic signal in a second direction through a downstream portion of the tubing. The signals are directed toward and can be received by respective ultrasonic receivers 374A, 374B on opposite sides of the transmitter 372. Feeding set 305 can be loaded on the pump 301 such that the upstream portion of the tubing 311 is disposed between the transmitter 372 and receiver 374A, and the downstream portion of the tubing is disposed between the transmitter and receiver 374B. Upon receipt of the ultrasonic signals, receivers 374A, 374B may detect the presence of fluid within the tubing 311 and/or a viscosity of the fluid based on the characteristics (e.g., signal amplitude) of the ultrasonic signal. The receivers 374A, 374B may also detect other conditions of the feeding set 305.

Figure 11:
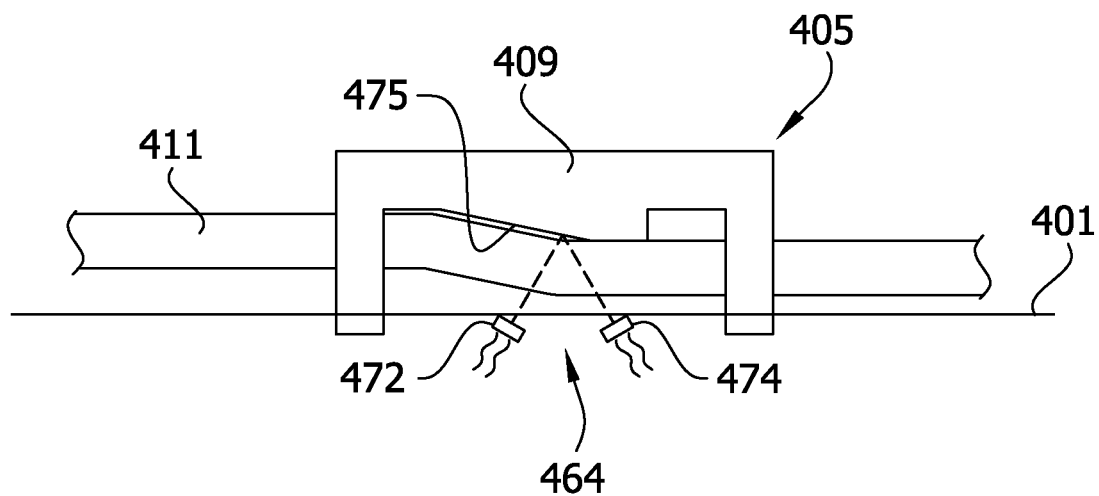
FIG. 11 is a schematic illustration of even another version of an enteral feeding pump and a fragmentary portion of a feeding set received on the pump.

Referring to FIG. 11, a pump 401 of a fifth version may comprise a sensor 464 including an ultrasonic transmitter 472 and an ultrasonic receiver 474 disposed underneath a feeding set 405 when the feeding set is received by the pump. The ultrasonic transmitter 472 may transmit an ultrasonic signal toward the feeding set 405 through tubing 411 of the feeding set. The feeding set 405 may include a cassette 409 having a reflective inner surface 475 that reflects the ultrasonic signal back through the tubing 411 toward the ultrasonic receiver 474. The reflective surface 475 may also be angled to direct the ultrasonic signal emitted from the transmitter 472 toward the receiver 474. This configuration allows for more varied pump designs since the tubing 411 does not have to be placed between the transmitter 472 and receiver 474. By placing the tubing 411 over the sensor 464 the loading process of the feeding set 405 can be simplified thus making the loading process more easily repeatable without error. Moreover, the overall configuration of the pump 401 is not overly constrained by the incorporation of the sensor 464.

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, the microprocessor 62 executes computer-executable instructions such as those illustrated in the figures to implement aspects of the invention. Aspects of the invention may also be practiced in distributed computing environments where tasks are performed by remote processing devices linked through a communications network. In a distributed computing environment, program modules may be located in both local and remote computer storage media including memory storage devices.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A flow control apparatus adapted to receive a feeding set, said flow control apparatus comprising:
 a housing capable of receiving at least a portion of the feeding set;
 a pumping device associated with the housing and positioned to contact the feeding set when the feeding set is received by the housing so the pumping device acts on the feeding set to produce fluid flow in the feeding set for delivery of fluid to a subject;
 an ultrasonic sensor arranged with respect to the pumping device to produce a sensor signal indicative of a viscosity of the fluid delivered through the feeding set; and
 a control circuit in communication with the ultrasonic sensor for receiving the sensor signal from the sensor indicative of the viscosity of the fluid and in communication with the pumping device to control operation thereof, the control circuit being configured to determine a representation of the viscosity of the fluid from the sensor signal and to operate the pumping device to produce a fluid flow rate based on the representation of the viscosity, wherein the control circuit is configured to determine the viscosity by analyzing an amplitude of the sensor signal.

2. The flow control apparatus set forth in claim 1 wherein the control circuit includes a memory containing a lookup table associating sensor signal amplitude with viscosity.

3. The flow control apparatus set forth in claim 1 wherein the pumping device comprises a motor and a rotor, the motor being adapted to rotate the rotor so that the rotor repeatedly contacts the feeding set to produce fluid flow through the feeding set, the control circuit adjusting a rotation rate of the rotor based on the viscosity of the fluid.

4. The flow control apparatus set forth in claim 3 wherein the control circuit is configured to decrease the rotation rate of the rotor as the detected fluid viscosity increases.

5. A flow control system for delivering fluid to a subject through a feeding set, comprising:
 a flow control apparatus including a pumping device configured to act on the feeding set to produce fluid flow in the feeding set for delivery of fluid to a subject; and
 an ultrasonic sensor arranged with respect to the pumping device and to sense the feeding set, the ultrasonic sensor including an ultrasonic emitter configured to emit an ultrasonic signal and an ultrasonic detector configured to detect the ultrasonic signal;
 a portion of the feeding set being disposed in a path of the ultrasonic signal producing a signal detectable by the ultrasonic detector providing an indication of a condition of the feeding set; and
 a control circuit in communication with the ultrasonic sensor and configured to identify the feeding set based on the sensor signal received from the ultrasonic sensor, wherein the control circuit includes a memory containing a plurality of identities of feeding sets, the control circuit being configured to match the sensor signal with one of the plurality of stored identities and to control operation of the flow control apparatus based on one or more characteristics associated with the stored identity that matches the sensor signal.

6. The flow control system set forth in claim 5 wherein the control circuit is configured to inhibit operation of the pumping device if the feeding set identified based on the sensor signal does not match a feeding set identity stored in the memory.

7. The flow control system set forth in claim 5 wherein the feeding set comprises tubing and a sensor component mounted on the tubing, the sensor component being disposed in the path of the ultrasonic signal when the feeding set is received by a housing configured to support the pumping device, the sensor component being constructed to produce the signal.

8. The flow control system set forth in claim 7 where the signal is produced by one of a size, shape, or material of the sensor component.

9. A flow control apparatus adapted to receive a pump set for driving fluid flow through the pump set, said flow control apparatus comprising:
   a housing capable of receiving at least a portion of the pump set;
   a pumping device supported by the housing and positioned to contact the pump set when the pump set is received by the housing so the pumping device acts on the pump set to produce fluid flow in the pump set; and
   a sensor assembly supported by the housing and arranged with respect to the pumping device for detecting a condition of the pump set when the pump set is received by the housing, the sensor assembly comprising a single emitter for emitting a signal and a plurality of detectors for detecting the signal emitted by the single emitter, each detector being configured to detect a different condition of the pump set based on the signal detected by the detectors, the sensor assembly comprising at least three detectors, a first detector detecting whether the pump set is properly received by the housing, a second detector detecting the type of pump set, and a third detector detecting a viscosity of the fluid in the pump set.

10. The flow control apparatus set forth in claim 9 wherein the sensor assembly is an ultrasonic sensor assembly including a single ultrasonic emitter and a plurality of ultrasonic detectors.

11. A flow control apparatus adapted to receive a pump set for delivering fluid through the pump set, said flow control apparatus comprising:
   a housing capable of receiving at least a portion of the pump set;
   a pumping device supported by the housing and positioned to contact the pump set when the pump set is received by the housing so the pumping device acts on the pump set to produce fluid flow in the pump set;
   an emitter constructed and arranged with respect to the pumping device to emit a first signal in a first direction toward a first section of the pump set when the pump set is received by the housing, and to emit a second signal in a second direction different from the first direction toward a second section of the pump set, the first and second signals being used to indicate a condition of the pump set at the first and second sections; and
   a first detector arranged with respect to the emitter for detecting the first signal, and a second detector arranged with respect to the emitter for detecting the second signal, the first and second detectors being disposed on opposite sides of the emitter such that the first direction extends opposite to the second direction.

12. The flow control apparatus set forth in claim 11 wherein the emitter is disposed to emit the first signal toward an upstream portion of the pump set and to emit the second signal toward a downstream portion of the pump set when the pump set is received by the housing.

13. The flow control apparatus set forth in claim 12 wherein the emitter is disposed between the upstream and downstream portions of the pump set when the pump set is received by the housing.

14. The flow control apparatus set forth in claim 11 wherein the emitter is disposed between the first and second detectors.

15. The flow control apparatus set forth in claim 11 wherein the first and second signals emitted from the emitter are ultrasonic signals, the signals detected by the detectors indicating the presence of fluid in the pump set.

* * * * *